United States Patent [19]

Vannice et al.

[11] 4,042,614
[45] Aug. 16, 1977

[54] HYDROCARBON SYNTHESIS FROM CO AND $H_2$ USING RU SUPPORTED ON A TITANIUM OXIDE

[75] Inventors: M. Albert Vannice, Plainfield; Robert L. Garten, Summit, both of N.J.

[73] Assignee: Exxon Research and Engineering Co., Linden, N.J.

[21] Appl. No.: 673,356

[22] Filed: Apr. 5, 1976

[51] Int. Cl.$^2$ .................................................. C07C 1/04
[52] U.S. Cl. .................................. 260/449 R; 252/460; 252/466 R
[58] Field of Search .......................... 260/449 R, 449.6

[56] References Cited

U.S. PATENT DOCUMENTS

| | | | |
|---|---|---|---|
| 2,464,532 | 3/1949 | Sellers | 260/449.6 |
| 2,637,739 | 5/1953 | McGrath | 260/449.6 |
| 2,699,988 | 1/1955 | McGrath et al. | 260/449.6 X |
| 2,850,515 | 9/1958 | Riblett et al. | 260/449.6 |

OTHER PUBLICATIONS

Shultz et al., Report of Investigations, 6974, Bureau of Mines, 1967, pp. 1-3, 5-14, 18.
Karn et al., I & EC, Product Res & Dev., 4, No. 4, (1965) pp. 265-269.
Pichler, Brennstoff-Chemie, 19, 226-230, 1938.
Kratel, Doctoral Dissertation, Technical University Berlin-Charlottenburg, 1937, Kasser Wilhem Inst. at Mulheim-Ruhr pp. 17-35.

*Primary Examiner*—Howard T. Mars
*Attorney, Agent, or Firm*—Joseph J. Allocca; Ernest A. Forzano

[57] ABSTRACT

A new method for the synthesis of hydrocarbons with chain lengths of from 2 to 10 carbon atoms inclusive and for selective generation of olefinic hydrocarbons in this carbon number range with reduced wax formation, said products being synthesized from CO and $H_2$ at pressures of from 100 to 3100 kPa which method comprises the steps of passing a synthesis gas stream of CO and $H_2$ at a $H_2$/CO ratio of from 0.1-10 at a space velocity of from 100 hr$^{-1}$ to 50,000 hr$^{-1}$ over a catalyst comprising from 0.01 to 15 wt. % ruthenium on $TiO_2$, other titanium-containing oxides or mixtures of said titanium-containing oxides for a time sufficient to effect the generation of desired olefinic hydrocarbon products, at a temperature of from 100° to 500° C and a pressure of from 100 to 10$^5$ kPa (1-1000 atm). The supported ruthenium catalyst has a BET surface area of from 10 to 60 m$^2$g$^{-1}$ of total catalyst with a ruthenium crystallite size of preferably less than 5 nm (50 A).

23 Claims, No Drawings

HYDROCARBON SYNTHESIS FROM CO AND H₂ USING Ru SUPPORTED ON A TITANIUM OXIDE

Ruthenium supported on $TiO_2$, other titanium-containing oxides or mixtures of titanium oxides results in a catalyst system which exhibits superior hydrocarbon synthesis characteristics. Such supported ruthenium catalysts exhibit selectivity to olefinic products of from 2 to 10 carbons inclusive in processes for olefin generation accompanied by greater product yields and exhibit improved longevity and tolerance to sulfur, activity maintenance, resistance to ruthenium volatilization in oxidizing atmospheres which might be encountered during catalyst regeneration and reduced wax formation in the synthesis process.

Ruthenium catalysts have been known for 50 years to be the most active of the Group VIII metals in the $CO/H_2$ synthesis reaction. It was discovered by Pichler (see H. Pichler, Brennstoff-Chem. 19, 226 (1938), H. Pichler and H. Buffleb, Brennstoff-Chem. 21, 247, 273, 285 (1940)) in 1938 that Ru can produce at low temperatures and very high pressures high molecular weight paraffinic waxes. Because it is such a good hydrogenation catalyst, ruthenium has not been noted for its capability to produce olefins. This is shown by the only study conducted under typical synthesis conditions using supported Ru where at 2160 kPa, 220°-240° C, and $H_2/CO$ ratios of 1 to 3, it was noted that the hydrocarbon product contained only "moderate" amounts of olefins (see F. S. Karn et al, I&EC Product Res. & Devel. 4, 265 (1965)). At a $H_2/CO$ ratio of 1, over 85 wt. % of the hydrocarbon product was composed of $C_5^+$ material. In addition, at 100 kPa and 222° C methane was the only hydrocarbon product observed. It is clear then that typical Ru catalysts would be expected to produce primarily high molecular weight paraffins at moderate pressures and methane as the principal product at atmospheric pressure.

Because it is so expensive, only supported, highly dispersed Ru catalysts can be considered for any commercial synthesis process since only in this state can the catalytic activity of most, if not all, of the Ru atoms be utilized. It is necessary then to prepare these catalysts in such a way that they possess a large Ru surface area thereby reducing the weight loading of Ru required to achieve the desired activity. Since it is now possible to produce catalysts in this manner, they may now be seriously considered as candidates for the commercial synthesis of olefins and paraffins from CO and $H_2$.

DESCRIPTION OF THE INVENTION

A new method for the selective synthesis of olefinic hydrocarbons and particularly olefins of from $C_2$ to $C_{10}$ chain length inclusive from CO and $H_2$ at pressures of from 100 to 3100 kPa which method comprises the steps of passing a synthesis gas stream comprising CO and $H_2$ at a $H_2/CO$ ratio of from 0.1-10, preferably 0.5-4, most preferably 1-3 at a space velocity of from 100 hr$^{-1}$ to 50,000 hr$^{-1}$ over a catalyst comprising from 0.01 to 15 wt. % ruthenium on $TiO_2$, other titanium-containing oxides or mixtures thereof for a time sufficient to effect the generation of desired olefinic hydrocarbon products at a temperature of from 100° to 500° C, preferably 150°-400° C, most preferably 150°-300° C and a pressure of from 100 to 10$^5$ kPa, preferably 100-3100 kPa, most preferably, 100-2060 kPa. The supported ruthenium catalyst system used in the instant process has a total BET surface area of from 10 to 60 m$^2$g$^{-1}$ with a ruthenium crystallite size of preferably less than 5 nm.

Ruthenium supported on $TiO_2$, other titanium-containing oxides or mixtures of titanium oxides results in a catalyst system which exhibits superior hydrocarbon synthesis characteristics in synthesis processes. The titanium-containing oxide supports which may be used in the practice of this invention are oxides having surface areas of from 1 to 200 m$^2$g$^{-1}$, preferably 10-100 m$^2$g$^{-1}$, most preferably, 25-100 m$^2$g$^{-1}$. The oxides are selected from the group comprising $TiO_2$, $Al_2O_3$-$TiO_2$, $SiO_2$-$TiO_2$, $TiO_2$-Carbon, $ZrTiO_4$, alkaline earth titanates ($BaTiO_3$, $CaTiO_3$, $SiTiO_3$, $MgTiO_3$) alkali titanates ($Na_2TiO_3$, $Li_2TiO_3$, $K_2TiO_3$) and rare earth titanates, preferably, the titanium oxide $TiO_2$. With most supported metal catalysts, the higher the surface area of the support, the higher the dispersion of the supported metal at a given metal loading. It is therefore, desirable to use a $TiO_2$ with as high a surface area as possible to maximize the dispersion of the ruthenium metal. However, when working with $TiO_2$, samples with surface areas of 150 to 250m$^2$g$^{-1}$ (usually prepared by precipitation techniques) desurface on heating to ~500° C. Commercially available $TiO_2$ made by flame hydrolysis of $TiCl_4$ has a stable surface area of ~60 m$^2$g$^{-1}$ for thermal treatments at temperatures of ~500° C and is therefore the preferred support. For thermal treatments at temperatures below 500° C, $TiO_2$ prepared by precipitation techniques may be successfully employed. Ruthenium is deposited on the chosen support in a concentration of from 0.01 to 15 wt. %, preferably 0.1 to 10 wt. %, most preferably 0.5 to 5 wt. %, with the ruthenium possessing a crystallite size, as determined by standard techniques such as X-ray diffraction or transmission electron microscopy of from 1 to 20 nm, preferably 1-10 nm, most preferably 1-5 nm.

Using standard experimental techniques, for a ruthenium on $TiO_2$ system, reduced in hydrogen at 450° C, X-ray diffraction shows no particles of Ru in the reduced catalyst which indicates particles having crystallite sizes of less than 5 nm, which corresponds to a dispersion of greater than 20%.

Ruthenium catalysts supported on $TiO_2$, other titanium-containing oxides, or mixtures thereof, exhibit selectivity to olefin products, especially $C_2$-$C_{10}$ inclusive olefins. Such catalysts, when used in the present system, exhibit improved selectivity to said olefins, improved longevity and tolerance to sulfur and resistance to ruthenium volatilization in oxidizing atmospheres as compared with ruthenium catalysts of the prior art which are supported on materials such as $Al_2O_3$, $SiO_2$ or carbon.

The ruthenium catalysts employed in the practice of the instant process are themselves prepared by techniques known in the art for the preparation of other catalysts systems, such as Ru on $Al_2O_3$, etc. A suitable ruthenium salt, such as ruthenium chloride, ruthenium nitrate or ruthenium acetate, etc., is dissolved in a solvent such as water or any suitable solvent and stirred with the chosen titanium oxide system. Preferably, the support is $TiO_2$ prepared by flame hydrolysis of $TiCl_4$, which $TiO_2$ has a surface area of ~60 m$^2$g$^{-1}$. After thorough mixing the mixture is allowed to dry and then heat treated in air at a temperature of from 100 to 150° C or alternatively may be dried immediately by heating in air at a temperature of between 100° to 150° C for several hours.

The final step however, is the essential step of heat treating the supported ruthenium catalyst, prepared as outlined above, or by similar techniques, in a reducing atmosphere such as hydrogen at a temperature greater than 300° C, preferably greater than 400° C, most preferably, greater than 500° C, for about 0.5 to 4 hours, preferably 1-2 hours.

EXAMPLE 1

Ruthenium catalysts with improved selectivity to olefin products and to hydrocarbons with carbon chain lengths of two carbons to ten carbons are obtained by depositing ruthenium on $TiO_2$ or titanium-containing oxide supports. Thus, a 2% $Ru/TiO_2$ catalyst is prepared by stirring together 10 grams of $TiO_2$ and 3ml of $RuCl_3$ solution containing 0.2 g of ruthenium. The $TiO_2$ is prepared by the flame hydrolysis of $TiCl_4$ to give a support with 60 $m^2g^{-1}$ surface area. Titania made by other techniques such as precipitation and calcination of a suitable salt is also satisfactory. After thoroughly mixing the $TiO_2$ and ruthenium solution, the mixture is dried overnight in air at 110°-120° C.

To illustrate the desirable properties of $Ru/TiO_2$ catalysts, they were compared to ruthenium supported on conventional supports such as $Al_2O_3$ or carbon. Thus, a 5% $Ru/\eta$-$Al_2O_3$ catalyst was prepared by thoroughly mixing 5.26 ml of $RuCl_3$ solution containing 0.526 grams of ruthenium with 10 grams of $\eta$-$Al_2O_3$. The resulting mixture was dried overnight in air at 110°-120° C. A 4% Ru/carbon catalyst was prepared by thoroughly mixing 6 ml of $RuCl_3$ solution containing 0.12 grams of ruthenium with 3 grams of carbon with a surface area of ~ 1000 $m^2g^{-1}$. The resultant mixture was dried overnight in air at 110°-120° C.

The desirable selectivity characteristics of $TiO_2$ or titanium-containing oxide-supported ruthenium catalysts compared to other supports is demonstrated in Tables I, II and III. At 103 kPa total pressure $Ru/TiO_2$ shows a markedly different product distribution than $Ru/Al_2O_3$. The formation of methane and very high molecular weight hydrocarbons is suppressed over the $Ru/TiO_2$ catalysts giving a product spectrum in which the carbon chain length range of two to five carbon atoms is maximized. For $Ru/Al_2O_3$, much more methane and higher molecular weight hydrocarbons are produced. $Ru/TiO_2$ also possesses the desirable characteristic that a large fraction of the $C_2$-$C_5$ products are olefinic. Thus, this catalyst is particularly suitable for producing from CO and $H_2$ a product stream which is highly olefinic and with carbon chain lengths of two to five carbon atoms. Olefins such as ethylene, propylene, butenes and pentenes in this range are particularly desirable as chemical intermediates for the production of plastics, rubber, alcohols, ketones and aldehydes, esters and acids.

Table II illustrates the desirable selectivity characteristics of $TiO_2$ or titanium-containing oxide-supported ruthenium catalysts at higher total pressures of reactants. At $10^3$ kPa the $Ru/TiO_2$ makes less methane and $C_8+$ hydrocarbons than $Ru/Al_2O_3$ with most of the products from $Ru/TiO_2$ being in the $C_2$ to $C_7$ carbon number range. $Ru/TiO_2$ thus exhibits improved selectivity to the desirable $C_2$ to $C_7$ hydrocarbons. Table II also illustrates the improved selectivity to olefins of $Ru/TiO_2$ compared to $Ru/Al_2O_3$. In the $C_2$ to $C_5$ carbon number range 42% of the products are olefins with $Ru/TiO_2$ whereas only 25% are olefins with $Ru/Al_2O_3$. $Ru/TiO_2$ is thus more selective for the production of the desirable olefins with carbon chain lengths of two to five carbon atoms.

Table III compares $Ru/TiO_2$ with ruthenium on a variety of other supports. Ruthenium supported on $TiO_2$ or titanium-containing oxide supports produces 42 wt. % of the products with carbon chain lengths of two to five carbon atoms, while ruthenium on $Al_2O_3$, carbon or ruthenium metal produce only 31%, 2% and 25%, respectively of products in this carbon number range. In addition, the fraction of olefins in the products is greatest for $Ru/TiO_2$ as indicated by the ethylene/ethane ratios for each catalyst. Ruthenium on $Al_2O_3$ or carbon, or unsupported ruthenium metal produce little or no ethylene in the $C_2$ fraction from CO and $H_2$ under the reaction conditions used in Table III whereas $Ru/TiO_2$ produces about one-half of the $C_2$ reaction as ethylene.

TABLE I

Selectivity of Ruthenium Catalysts
(Reaction Conditions: $H_2CO$ = 1, Pressure = 103 kPa)

| Catalyst[a] | Temp. (° C) | % CO Conv. | Product Carbon Number | Total wt % | wt % Olefin | wt % Paraffin |
|---|---|---|---|---|---|---|
| 2% $Ru/TiO_2$ | 262 | 0.7 | $C_1$ | 26 | — | — |
| | | | $C_2$ | 17 | 12 | 5 |
| | | | $C_3$ | 28 | 20 | 8 |
| | | | $C_4$ | 19 | 15 | 4 |
| | | | $C_5$ | 10 | 7 | 3 |
| | | | $C_6+$ | — | — | — |
| 5% $Ru/Al_2O_3$ | 267 | 1.7 | $C_1$ | 47 | — | — |
| | | | $C_2$ | 13 | 5 | 8 |
| | | | $C_3$ | 21 | — | — |
| | | | $C_4$ | 7 | 6 | 1 |
| | | | $C_5$ | 6 | — | — |
| | | | $C_6+$ | 5 | — | — |

(1 atm = 103 kPa)
[a]Each catalyst reduced 1 hour at 450° C prior to introducing feed at the reaction temperature.

TABLE II

Selectivity of Ruthenium Catalysts
(Reaction Conditions: $H_2$/CO = 1, Pressure = 980 kPa)

| Catalyst[a] | Temp. (° C) | % CO Conv. | Product Carbon Number | Total wt % | Wt % Olefin | Wt. % Paraffin |
|---|---|---|---|---|---|---|
| 2% $Ru/TiO_2$ | 267 | 7 | $C_1$ | 14 | — | — |
| | | | $C_2$ | 6 | 2 | 4 |
| | | | $C_3$ | 21 | 14 | 7 |
| | | | $C_4$ | 20 | 16 | 4 |
| | | | $C_5$ | 17 | 10 | 7 |
| | | | $C_6$ | 13 | 8 | 5 |
| | | | $C_7$ | 9 | 5 | 4 |
| | | | $C_8+$ | — | — | — |
| 5% $Ru/\eta$-$Al_2O_3$ | 274 | 10 | $C_1$ | 24 | — | — |
| | | | $C_2$ | 6 | 1 | 5 |
| | | | $C_3$ | 16 | 12 | 4 |
| | | | $C_4$ | 11 | 6 | 5 |
| | | | $C_5$ | 12 | 6 | 6 |
| | | | $C_6$ | 11 | — | — |
| | | | $C_7$ | 9 | — | — |
| | | | $C_8+$ | 12 | — | — |

(1 atm = 103 kPa)
[a]Each catalyst reduced 1 hour at 450° C prior to introducing feed at the reaction temperature.

TABLE III

Selectivity of Ruthenium Catalysts
(Reaction Conditions: $H_2/CO = 3$, Pressure = 103 kPa)

| Catalyst | T°C | % CO Conv. | CH$_4$ | C$_2$H$_4$ | C$_2$H$_6$ | C$_3$H$_6$ C$_3$H$_8$ | C$_4$H$_8$ C$_4$H$_{10}$ | C$_5$H$_{10}$ C$_5$H$_{12}$ | C$_6$+ |
|---|---|---|---|---|---|---|---|---|---|
| 2% RuTiO$_2$[a] | 228 | 1.8 | 54 | 6 | 5 | 16 | 10 | 5 | 4 |
| 5% Ru/Al$_2$O$_3$[a] | 229 | 10.6 | 66 | 1 | 9 | 6 | 9 | 6 | 4 |
| 4% Ru/Carbon[b] | 234 | 1.6 | 98 | 0 | 2 | 0 | 0 | 0 | 0 |
| Ru Metal Powder[c] | 217 | 27.1 | 74 | 0 | 13 | 8 | 3 | 1 | 1 |

[a] Catalysts reduced for 1 hour at 450° C before feed introduced.
[b] Catalyst reduced 1 hour at 400° C before feed introduced.
[c] Catalyst reduced 1 hour at 300° C before feed introduced.

What is claimed is:

1. A process for the selective synthesis of olefins from C$_2$ to C$_{10}$ chain length inclusive, said process comprising the steps of passing H$_2$ and CO at a H$_2$/CO ratio of 0.1 to 10 over a catalyst comprising ruthenium on a titanium-containing oxide support, wherein said titanium-containing oxide support is selected from the group consisting of TiO$_2$, ZrTiO$_4$, TiO$_2$-carbon, TiO$_2$-Al$_2$O$_3$, TiO$_2$-SiO$_2$, alkaline earth titanates, alkali titanates, rare earth titanates and mixtures thereof, at a space velocity of from 100 to 50,000 V/V/Hr. at a temperature of from 100° to 500° C., at a pressure of from 100 to 10$^5$ kPa for a time sufficient to effect the generation of the desired olefinic products in the desired ratio wherein the concentration of said ruthenium in said catalyst is from 0.01 to 15% by weight.

2. The process of claim 1 wherein the titanium-containing oxide is TiO$_2$.

3. The process of claim 1 wherein the titanium-containing oxide has a surface area of from 1 to 200 m$^2$g$^{-1}$.

4. The process of claim 2 wherein the TiO$_2$ has a surface area of from 25 to 100 m$^2$g$^{-1}$.

5. The process of claim 1 wherein the ruthenium concentration is from 0.5 to 5 wt. %.

6. The process of claim 1 wherein the catalyst consisting of ruthenium supported on a titanium-containing oxide has a ruthenium particle crystallite size of from 1 to 20 nm.

7. The process of claim 6 wherein the catalyst consisting of ruthenium supported on a titanium-containing oxide has a ruthenium particle crystallite size of less than 5 nm.

8. The process of claim 1 wherein the catalyst consisting of ruthenium supported on a titanium-containing oxide has a surface area of from 10 to 60 m$^2$g$^{-1}$.

9. The process of claim 1 wherein the H$_2$/CO ratio is 4.0 to 0.5, the temperature is from 150° to 400° C and the pressure is from 100 to 3100 kPa.

10. The process of claim 1 wherein the H$_2$/CO ratio is 3 to 1, the temperature is from 150° to 300° C and the pressure is from 100 to 2060 kPa.

11. The process of claim 2 wherein the ruthenium on titanium oxide catalyst has a weight loading of ruthenium of from 0.5 to 5 wt. % based on total catalyst.

12. The process of claim 2 wherein the ruthenium on titanium oxide catalyst has a ruthenium crystallite size of less than 5 nm (<50A).

13. The process of claim 3 wherein the titanium-containing oxide has a surface area of from 10 to 100 m$^2$g$^{-1}$.

14. The process of claim 3 wherein the titanium-containing oxide has a surface area of from 25 to 100 m$^2$g$^{-1}$.

15. The process of claim 1 wherein the ruthenium concentration is from 0.1 to 10 wt. %.

16. The process of claim 6 wherein the catalyst consisting of ruthenium supported on a titanium-containing oxide has a ruthenium particle crystallite size of from 1 - 10 nm.

17. The process of claim 2 wherein the TiO$_2$ has a surface area of from 1 - 200 m$^2$g$^{-1}$.

18. The process of claim 2 wherein the TiO$_2$ has a surface area of 10 - 100 m$^2$g$^{-1}$.

19. The process of claim 2 wherein the catalyst consisting of ruthenium supported on TiO$_2$ has a ruthenium particle crystallite size of from 1 - 20 nm.

20. The process of claim 19 wherein the catalyst consisting of ruthenium supported on TiO$_2$ has a ruthenium particle crystallite size of from 1 - 10 nm.

21. The process of claim 2 wherein the ruthenium on TiO$_2$ catalyst has a weight loading of ruthenium of from 0.1 to 10 wt. %, based on total catalyst.

22. The process of claim 2 wherein the H$_2$/CO ratio is 4.0 to 0.5, the temperature is from 150° to 400° C. and the pressure is from 100 to 3100 kPa.

23. The process of claim 2 wherein the H$_2$/CO ratio is 3 to 1, the temperature is from 150° to 300° C. and the pressure is from 100 to 2060 kPa.

* * * * *